United States Patent
Brasseur et al.

(10) Patent No.: US 7,910,584 B2
(45) Date of Patent: Mar. 22, 2011

(54) 3-SPIROINDOLIN-2-ONE DERIVATIVES, PREPARATION AND THERAPEUTIC USE THEREOF

(75) Inventors: Denis Brasseur, Chilly Mazarin (FR); Claudine Serradeil-Le Gal, Escalquens (FR); Gareth Shackleton, White Bay (GB)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/504,260

(22) Filed: Jul. 16, 2009

(65) Prior Publication Data

US 2009/0275579 A1   Nov. 5, 2009

Related U.S. Application Data

(63) Continuation of application No. 11/682,991, filed on Mar. 7, 2007, now abandoned, which is a continuation of application No. PCT/FR2005/002219, filed on Sep. 7, 2005.

(30) Foreign Application Priority Data

Sep. 9, 2004  (FR) .................................. 04 51997

(51) Int. Cl.
*A61K 31/535* (2006.01)
*C07D 413/12* (2006.01)
(52) U.S. Cl. .................... 514/235.2; 544/144
(58) Field of Classification Search .............. 544/144; 514/235.2
See application file for complete search history.

(56) References Cited

U.S. PATENT DOCUMENTS

| 5,994,350 A | 11/1999 | Foulon et al. |
| 6,046,341 A | 4/2000 | Foulon et al. |
| 2007/0191367 A1* | 8/2007 | Brasseur et al. ........... 514/237.2 |

OTHER PUBLICATIONS

Byrn, et. al., Solid State Chemistry of Drugs. Second Edition, (1999), pp. 233-247.
Bolignano. D., et. al., Aquaretic Agents: What's Beyond the Treatment of Hyponatremia?; Current Pharmaceutical Design, (2007), vol. 13, pp. 865-871.

* cited by examiner

*Primary Examiner* — Rebecca L Anderson
(74) *Attorney, Agent, or Firm* — Barbara E. Kurys; Ronald G. Ort

(57) ABSTRACT

The subject of the present invention is a compound of formula (I):

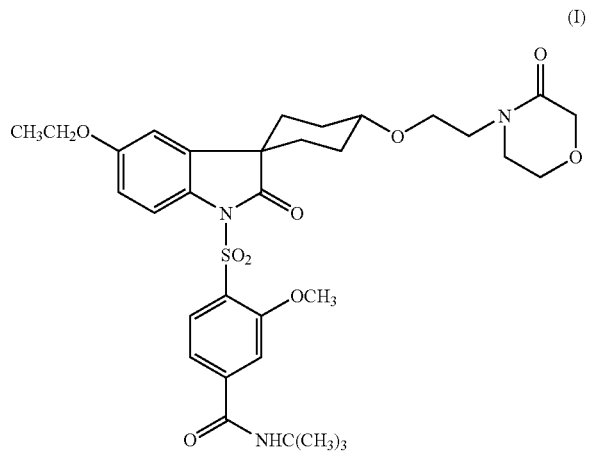

in the base, hydrate or solvate state, in the form of cis/trans isomers or of mixtures thereof, preparation and therapeutic use thereof.

3 Claims, No Drawings

3-SPIROINDOLIN-2-ONE DERIVATIVES, PREPARATION AND THERAPEUTIC USE THEREOF

The present invention relates to 3-spiroindolin-2-one derivatives, to the process for preparing them and to the therapeutic use thereof.

A subject of the present invention is compounds of formula (I):

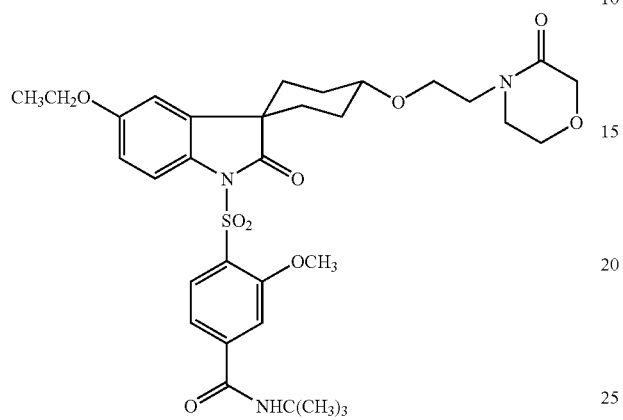

in the base, hydrate or solvate state, in the form of cis/trans isomers or of mixtures thereof.

The compounds of formula (I) contain one or more rings. They can therefore exist in the form of cis/trans isomers. These isomers and mixtures thereof are part of the invention.

The compounds of formula (I) can also exist in hydrate and/or solvate form, i.e. in the form of an association or of a combination with one or more molecules of water or with a solvent. Such hydrates and solvates are also part of the invention.

The compounds of the invention can be prepared according to scheme 1 which follows.

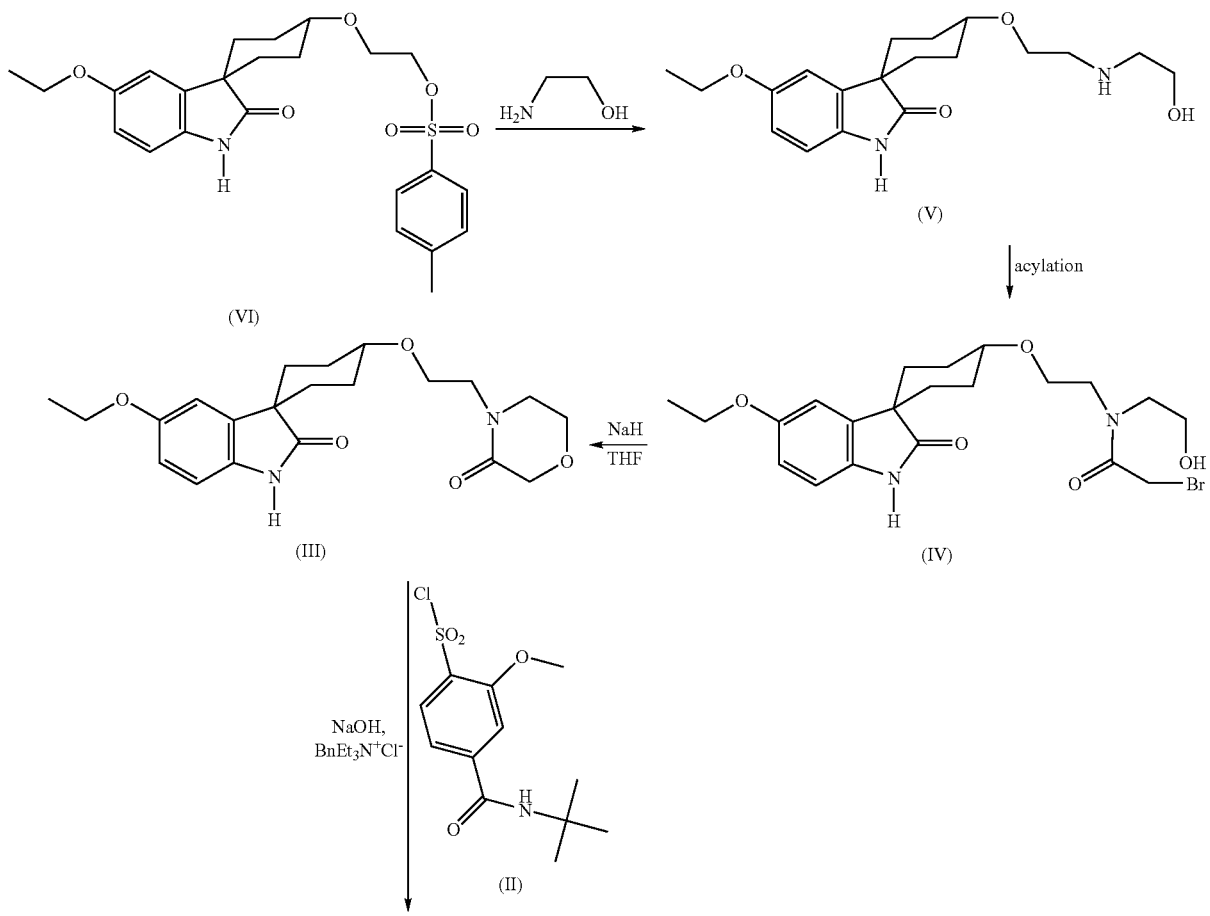

-continued

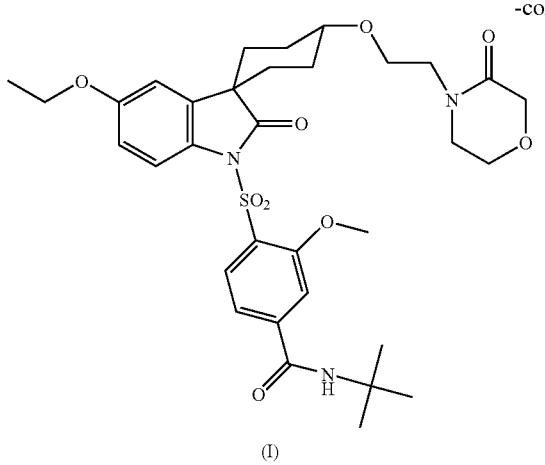
(I)

According to scheme 1, the compound of formula (V) is obtained by means of a step consisting of displacement of the tosylate group present in the compound of formula (VI), by an ethanolamine group, in the presence of a protic solvent such as ethanol or methanol. The synthesis of the compound for formula (VI) is described in document EP 0 873 309 (preparation 4, compound (III.4)). The compound of formula (V) is subsequently converted to the compound of formula (IV) by means of a reaction consisting of acylation of the amine function with 2-bromoacetyl bromide or bromoacetyl chloride, in the presence of triethylamine and of an aprotic solvent such as dichloromethane ($CH_2Cl_2$) or tetrahydrofuran (THF). The compound of formula (IV) is then converted to the compound of formula (III) by means of a cyclization reaction in a basic medium, in the presence of a polar aprotic solvent such as THF, dimethyl-formamide or dimethyl sulfoxide. The compound of formula (III) thus obtained is added to the compound of formula (II), in a basic medium and in the presence of benzyltriethylammonium chloride and in an aprotic solvent such as $CH_2Cl_2$ or THF, so as to obtain the compound of formula (I). The synthesis of the compound of formula (II) is described in document EP 0 873 309 (preparation 13, reactant (2).2).

When the method of preparing the reactants is not described, they are commercially available or are described in the literature, or else they can be prepared according to methods which are described therein or which are known to those skilled in the art.

The example which follows describes a method of preparing a compound in accordance with the invention. This example is not limiting and merely illustrates the present invention.

In the example of preparation of a compound of formula (I) which follows, the following definitions are used:
DMSO=dimethyl sulfoxide,
LC/MS=liquid chromatography/mass spectrometry,
Mp=melting point,
eq.=molar equivalent,
s=singlet,
m=multiplet,
t=triplet.

The $^1H$ and $^{13}C$ NMR spectra were realized on two Bruker devices: AC 200 and Avance 600.

The chromatography/mass spectrometry procedures were carried out on a Micromass® "TOF" (time of flight) mass spectrometer, model LCT.

The melting points were measured on a Büchi melting point B-545 device.

EXAMPLE

Stage a): Displacement of the Tosylate by Ethanolamine (Preparation of the Compound of Formula (V))

6 ml of ethanolamine (6.1 g; 100 mmol; 5 eq.), 20 ml of methanol, and then 9.19 g of the compound of formula (VI) (20 mmol; 1 eq.), the synthesis of which is described in document EP 0 873 309 (preparation 4, compound (III.4)), are introduced into a 100 ml round-bottomed flask under an argon atmosphere. The reaction mixture is heated to reflux for 10 hours. After cooling, the reaction medium is concentrated under vacuum, and the residue is washed with water and extracted several times with ethyl acetate. The organic phases are combined, dried over sodium sulfate, filtered and concentrated.

In the subsequent step, the crude product obtained is used without purification.

The proton NMR spectrum is compatible with the desired structure.

The LC/MS analysis confirms the predominant formation of the product: $M+H^+=349.5$.

Stage B): Acylation of the Amine Function with 2-Bromo-Acetyl Bromide (Preparation of the Compound of Formula (IV))

7.45 g of the animated derivative of formula (V) obtained in stage a) (19.24 mmol; 1 eq.), 19.5 ml of anhydrous dichloromethane and 2.68 ml of triethylamine (1.94 g; 19.24 mmol; 1 eq.) are introduced into a 100 ml round-bottomed flask under an argon atmosphere. After cooling of the reaction medium to −15° C. (methanol/ice bath), 1.71 ml of 2-bromoacetyl bromide (3.96 g; 19.24 mmol; 1 eq.) are added in 30 minutes. The temperature of the medium is brought back up to ambient temperature and the reaction is stirred for 2 hours. The mixture is subsequently washed with water and the aqueous phase is extracted several times with dichloromethane. The organic phases are combined, subsequently dried over magnesium sulfate, filtered, and concentrated. The crude product (8.26 g) is purified on silica gel (320 g; 40-63 μm particles; the eluent used is a gradient: pure $CH_2Cl_2$ to a 95/5

CH$_2$Cl$_2$/methanol mixture). The fractions containing the desired derivative are combined and concentrated under vacuum.

The proton NMR spectrum is compatible with the desired structure.

The LC/MS analysis confirms the structure of the desired product: M+H+ in the form of a doublet in a ratio 1/1=469.3/471.3.

Stage C): Formation of the Morpholinone Ring (Preparation of the Compound of Formula (III))

1.93 g of the brominated derivative (4.13 mmol; 1 eq.) of formula (IV) obtained in stage b), 100 ml of anhydrous tetrahydrofuran, then 165 mg of sodium hydride (at 60% as a dispersion in oil; 4.13 mmol; 1 eq.) are introduced into a 250 ml round-bottomed flask under an argon atmosphere. The reaction medium is stirred vigorously at ambient temperature for 4 hours. The mixture is subsequently washed with water and the aqueous phase is extracted several times with dichloromethane. The organic phases are combined, subsequently dried over magnesium sulfate, filtered, and concentrated. The crude product (1.73 g) is purified on silica gel (110 g; 40-63 μm particles; the eluent used is a gradient: pure CH$_2$Cl$_2$ to a 96/4 CH$_2$Cl$_2$/methanol mixture). The fractions containing the desired derivative are combined and concentrated under vacuum.

The $^1$H and $^{13}$C NMR spectra are compatible with the desired structure.

The LC/MS analysis confirms the structure of the product (M+H$^+$=389.4).

Stage D): Coupling Between Indolinone and Sulfonyl Chloride (Preparation of the Compound of Formula (I))

288 mg of the morpholinone derivative (0.74 mmol; 1 eq.) of formula (III) obtained in stage c), 4 ml of dichloromethane, 17 mg of benzyltriethylammonium chloride (0.07 mmol; 0.1 eq.) and 272 mg of the sulfonyl chloride derivative of formula (II), the preparation of which is described in document EP 0 873 309 (preparation 13, reactant (2).2) (0.89 mmol; 1.2 eq.) are introduced into a 25 ml round-bottomed flask under an argon atmosphere. After cooling of the reaction medium to −5° C. (salt water/ice bath), sodium hydroxide at 40% in water (57 mg solid NaOH; 1.43 mmol; 1.93 eq.) is added. The reaction medium is vigorously stirred at −5° C. for 2 hours and then at ambient temperature for a further 2 hours. The mixture is subsequently washed with water and the aqueous phase is extracted several times with dichloromethane. The organic phases are combined, subsequently dried over magnesium sulfate, filtered, and concentrated. The crude product obtained is purified on silica gel (40-63 μm particles; the eluent used is a gradient: pure CH$_2$Cl$_2$ to a 95/5 CH$_2$Cl$_2$/methanol mixture). The fractions containing the desired derivative are combined and concentrated under vacuum.

The $^1$H and $^{13}$C NMR spectra are compatible with the desired structure.

$^{13}$C NMR (150 MHz in DMSO D$_6$): 177.5; 166.4; 165.2; 157.1; 156.3; 143.6; 134.9; 131.4; 131.3; 127.1; 119.7; 114.5; 113.8; 112.4; 110.4; 79.5; 75.5; 67.8; 65.5; 63.9; 63.8; 56.7; 51.7; 47.7; 45.4; 31.4; 28.8; 26.4; 15.1.

$^1$H NMR (600 MHz in DMSO D$_6$): 8.0 (m, 2H); 7.5 (m, 3H); 7.05 (s, 1H); 6.85 (m, 2H); 4.0 (m, 4H): 3.8 (m, 2H); 3.6 (s, 3H); 3.55 (m, 2H); 3.45 (m, 5H): 1.75 (m, 8H); 1.35 (s, 9H): 1.3 (t, 3H).

The analysis by LC/MS confirms the structure of the desired product: M+H$^+$=658.

Mp=90° C.

The compounds according to the invention were subjected to pharmacological assays which show their advantage as active substances in therapy.

They were in particular tested with regard to their effects. More particularly, the affinity of the compounds of the invention for vasopressin V$_2$ receptors was determined in an in vitro binding assay according to the technique described below.

In the following text:
EDTA=ethylenediaminetetraacetic acid,
BSA=bovine serum albumin,
AVP=vasopressin,
DMSO=dimethyl sulfoxide.

In Vitro Affinity Measurement—IC$_{50}$:

The affinity of the compounds of the invention for vasopressin V$_2$ receptors was measured in in vitro binding assays, as described in *J. Pharmacol. Exp. Ther.*, (2002), 300, pp. 1122-1130.

Plasma membranes (approximately 20 μg/ml) originating from tissues or the CHO cell line expressing recombinant human vasopressin V$_2$ receptors are incubated for 45 minutes at 25° C. in 200 μl of TRIS-HCl buffer (50 mM; pH 8.2) containing 2 mM of MgCl$_2$, 1 mM of EDTA, 0.1% of BSA, 1 mg/ml of bacitracin and 3.5 nM of [H$^3$]-AVP. The reaction is stopped by filtration and washing over GF/B filters. The non-specific binding is determined in the presence of 1 μM of AVP. The compounds of the invention, dissolved beforehand at the concentration of 10$^{-2}$ M in DMSO, are tested in a dilution range.

For each concentration, the results are expressed as percentage inhibition of specific binding. An IC$_{50}$ (concentration of product that inhibits 50% of the specific binding) is determined for each of the products using the "RS1 binding" program (BBN Domain, Cambridge, Mass.).

These IC$_{50}$ values are generally less than 10$^{-8}$ M.

The compound obtained according to the previous example of the present invention has an IC$_{50}$ of approximately 7.3×10$^{-9}$ M.

The results of the biological assays show that the compounds have an affinity for V$_2$ receptors and are specific antagonists of this receptor.

The compounds according to the invention can be used for the preparation of medicaments, in particular V$_2$ receptor antagonist medicaments.

Thus, according to another of its aspects, a subject of the invention is medicaments which comprise at least one compound of formula (I).

Compounds that are vasopressin V$_2$ receptor antagonists exhibit aquaretic properties in animals and humans (*Cardiovascular Drug Review*, (2001), 3: pp. 201-214). Thus, the compounds according to the invention have a large range of therapeutic indications and can advantageously replace conventional diuretics in all pathologies where they are recommended in humans and in animals.

Thus, the compounds according to the invention may be of use in particular in the treatment and/or the prevention of central and peripheral nervous system conditions, cardiovascular system conditions, conditions of the endocrine and hepatic system, of the renal sphere, of the gastric, intestinal and pulmonary sphere, in ophthalmology, and in sexual behavior disorders, in humans and in animals.

More particularly, the compounds according to the invention can be used in the treatment and/or the prevention of various vasopressin-dependent conditions and also in vasopressin secretion dysfunctions such as the syndrome of inappropriate ADH secretion (or SIADH), cardiovascular conditions, such as hypertension, pulmonary hypertension, cardiac insufficiency, circulatory insufficiency, myocardial infarction, atherosclerosis or coronary vasospasm, in particular in smokers, unstable angina and percutaneous transluminal coronary angioplasty (or PTCA), cardiac ischemia, disturbances in hemostasis, in particular hemophilia, Von Willebrand syndrome; central nervous system conditions, migraine, cerebral vasospasm, cerebral hemorrhage, cerebral edema, depression, anxiety, bulimia, psychotic states, memory disorders, for example; rinopathies and kidney dysfunction such as edema, renal vasospasm, necrosis of the renal cortex, nephrotic syndrome, polycystic kidney disease (or PKD) in various forms in children and in adults, hyponatremia and hypokalemia, diabetes, Schwartz-Bartter syndrome or renal lithiasis; gastric system conditions, such as gastric vasospasm, portal hypertension, hepatocirrhosis, ulcers, the pathology of vomiting, for example nausea, including nausea due to chemotherapy, travel sickness, diabetes insipidus and enuresis; hepatic system conditions such as liver cirrhosis; abdominal ascites and all disorders that cause abnormal water retention; adrenal disorders (Cushing's disease), and in particular hypercorticism and hyperaldosteronemia. The compounds according to the invention can also be used in the treatment and/or the prevention of sexual behavior disorders, in conditions of being overweight or of excess weight and obesity by advantageously replacing the conventional diuretics already used for this indication. In women, the compounds according to the invention can be used for treating dysmenorrhea or premature labor. The compounds according to the invention can also be used in the treatment of small cell lung cancers, hyponatremic encephalopathies, Raynaud's disease, pulmonary syndrome and glaucoma, and in the prevention of cataracts, in post-operative treatments, in particular after abdominal, cardiac or hemorrhagic surgery, and in treatments for disorders or diseases of the inner ear, such as Meniere's disease, tinnitus, dizziness, hearing difficulties, in particular in the low-pitch range, or buzzing in the ears, hydrops, and in particular endolymphatic hydrops.

According to another of its aspects, the present invention relates to pharmaceutical compositions comprising, as active ingredient, at least one compound according to the invention. These pharmaceutical compositions contain an effective dose of at least one compound of formula (I) according to the invention, and also at least one pharmaceutically acceptable excipient.

Said excipients are chosen, according to the pharmaceutical form and the method of administration desired, from the usual excipients that are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its possible salt, solvate or hydrate, can be administered in unit administration form, as a mixture with conventional pharmaceutical excipients, to animals and to human beings for the prophylaxis or the treatment of the disorders or of the diseases above.

Suitable unit administration forms include oral administration forms, such as tablets, soft or hard gelatin capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in tablet form may comprise the following components:

| | |
|---|---:|
| Compound according to the example of the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

Said unit forms contain a dose so as to allow a daily administration of from 0.5 mg to 800 mg of active ingredient per individual, more particularly from 0.5 mg to 200 mg, according to the galenic form.

There may be cases where higher or lower dosages are appropriate; such dosages do not depart from the scope of the invention. According to the usual practice, the dosage suitable for each patient is determined by the physician according to the method of administration and the weight and response of said patient.

According to another of its aspects, the present invention also relates to a method of treating and/or preventing the pathologies indicated above, which comprises the administration, to a patient, of an effective dose of a compound according to the invention, or of a hydrate or solvate thereof.

What is claimed is:

1. A compound of formula (I):

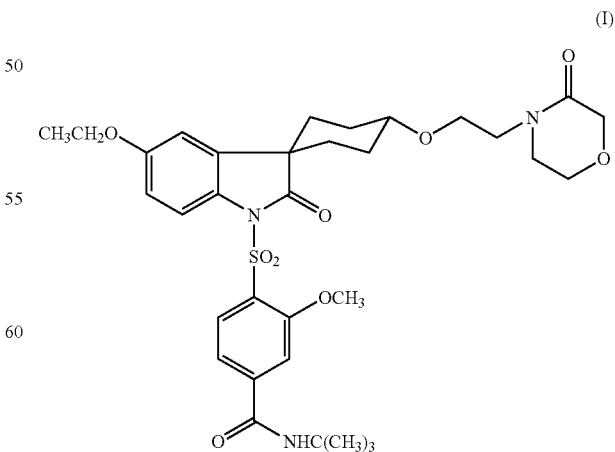

in the base form of cis/trans isomers or of mixtures thereof.

2. A process for preparing a compound as claimed in claim 1, the process comprising reacting a morpholinone derivative of formula (III)
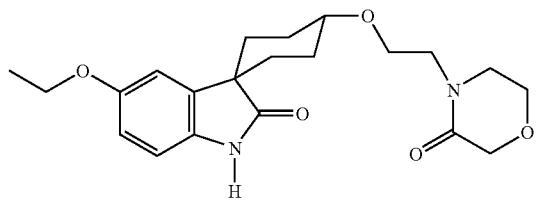
with a sulfonyl chloride of formula (II)
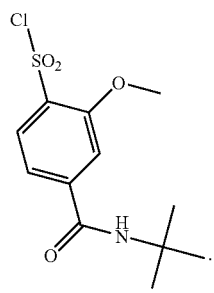
3. A pharmaceutical composition, comprising at least one compound as claimed in claim 1, and at least one pharmaceutically acceptable excipient.
* * * * *